United States Patent [19]
Lancaster

[11] Patent Number: 5,643,715
[45] Date of Patent: Jul. 1, 1997

[54] HUMAN PAPILLOMAVIRUS TYPE 52 DNA SEQUENCES AND METHODS FOR EMPLOYING THE SAME

[76] Inventor: Wayne D. Lancaster, 3763 Steiner Rd., Trenton, Mich. 48183

[21] Appl. No.: 217,015

[22] Filed: Mar. 23, 1994

Related U.S. Application Data

[63] Continuation of Ser. No. 972,355, Nov. 5, 1992, abandoned, which is a continuation of Ser. No. 262,597, Oct. 26, 1988, abandoned.

[51] Int. Cl.$^6$ .................... C12Q 1/70; C12N 15/37; C07H 21/02; C07H 21/04
[52] U.S. Cl. .................... 435/5; 435/6; 435/320.1; 536/23.72; 536/24.32
[58] Field of Search .................... 435/235.1, 5, 6; 536/23.1, 23.72, 24.32; 935/78

[56] References Cited

U.S. PATENT DOCUMENTS

| | | | |
|---|---|---|---|
| 4,849,331 | 7/1989 | Lorincz | 435/5 |
| 4,849,332 | 7/1989 | Lorincz | 435/5 |
| 4,849,334 | 7/1989 | Lorincz | 435/5 |
| 4,908,306 | 3/1990 | Lorincz | 435/5 |

OTHER PUBLICATIONS

Shimoda, K. et al. 1988, *Journal of General Virology* vol. 69 pp. 2925–2928.
Funahashi, S. et al.1989, *Journal of Cellular Biochemistry*, Sup. 13C, p. 226.
Cole, S. et al. 1986, *Journal of Virology*, vol. 58 pp. 991–995.
Lorincz, A. et al. 1986, *Journal of Virology*, vol. 58 pp. 225–229.
Seedorf, K. et al. 1985, *Virology*, vol. 145 pp. 181–185.
Dartmann, K. et al. 1986, *Virology*, vol. 151, pp. 124–130.
Schwarz, E. et al. 1983, *EMBO Journal*, vol. 2 pp. 2341–2348.
Burns, J. et al. 1987, *J. Clin. Pathol.* vol. 40 pp. 858–864.
Crum, C.P. et al. 1988, *Laboratory Investigation* vol. 58 pp. 354–359.
Landry, M.L. et al. 1985, *Clin. Lab. Med.* vol. 5 pp. 513–529.
Saito, J. et al. 1987, *Jpn. J. Cancer Res. (Gann)*, vol. 78 pp. 1081–1087.
American Type Culture Collection NIH Repository of Human, DNA Probes and Libraries, 1988. ATCC, Rockville, MD. pp. 66–68, 72, 116–119.
Szostak, J.W. et al. 1979. Meth. Enzymol vol. 68 pp. 419–428.
Arrand, J. 1985, In: Nucleic Acid Hybridization, ed. Hames, B.D. et al, IRL Press, Washington DC, pp. 17–45.
Tooze, J., *DNA Tumor Viruses*, 2nd Ed., Cold Spring Harbor Laboratories, pp. 371–382d (1981).
Gissman, L., *Cancer Surv.* 3:161–181 (1984).
Durst, M., et al., *Proc. Natl. Acad. Sci. USA* 80:3812–3815 (1983).
Boshart, M., et al., *EMBO J.* 3:1151–1157 (1984).
de Villiers, E.-M., et al., *J. Virol* 40: 932–935 (1981).
Gissmann, L., et al., *J. Virol* 44: 393–400 (1982).
Lorincz, A.T., et al., *J. Virol.* 58:225–229 (1986).
Beaudenon, S., et al., *Nature* 321:246–249 (1986).
Coggin, J.R., et al., *Canc. Res.* 39:545–546 (1979).
Gissmann, L., et al., *Proc. Natl. Acad. Sci. USA* 80:560–563 (1983).
Zachow, K.R., et al., *Nature* 300:771–773 (1982).
Rando, R.E., et al., *J. Virol* 57:353–356 (1986).
Heilman, C.A. et al. *J. Virol.* 36 :395–407 (1980).
Pfister, H., *Rev. Physiol. Biochem. Pharmacol.* 99:111–181 (1984).
Noda et al., The 7th International Papillomavirus Workshop, May 16–20, Nice, France (1988).

*Primary Examiner*—Mary E. Mosher

[57] ABSTRACT

Nucleic acid hybridization probes for human papillomavirus types and particularly human papillomavirus type 52; and methods for employing the same.

27 Claims, 4 Drawing Sheets

```
   1 ATAAGCAGAC CCAGTTATGC ATTTTAGGAT GCAAGCCTCC TATAGGTGAA CATTGGGGTA
  61 AGGGAACCCC TTGTAATAAT AATTCAGGAA ATCCTGGGGA TTGTCCTCCC CTACAGCTCA
 121 TTAACAGTGT AATACAGGAT GGGGACATGG TAGATACAGG ATTTGGTTGC ATGGATTTTA
 181 ATACCTTGCA AGCTATTAAA AGTGATGTGC CCATTGATAT ATGTAGCAGT GTATGTAAGT
 241 ATCCAGATTA TTTGCAAATG GCTAGCGAGC CATATGGTGA CAGTTTGTTC TTTTTTCTTA
 301 GACGTGAGCA AATGTTTGTT AGACACTTTT TTAATAGGGC CGGTACCTTA GGTGACCCTG
 361 TGCCAGGTGA TTTATATATA CAAGGGTCTA ACTCTGGCAA TACTGCCACT GTACAAAGCA
 421 GTGCTTTTTT TCCTACTCCT AGTGGTTCTA TGGTAACCTC AGAATCCCAA TTATTTAATA
 481 AACCGTACTG GTTACAACGT GCGCAGGGCC ACAATAATGG CATATGTTGG GGCAATCAGT
 541 TGTTTGTCAC AGTTGTGGAT ACCACTCGTA GCACTAACAT GACTTTATGT GCTGAGGTTA
 601 AAAAGGAAAG CACATATAAA AATGAAAATT TTAAGGAATA CCTTCGTCAT GGCGAGGAAT
 661 TTGATTTACA ATTTATTTTT CAATTGTGCA AAATTACATT AACAGCTGAT GTTATGACAT
 721 ACATTCATAA GATGGATGCC ACTATTTTAG AGGACTGGCA ATTTGGCCTT ACCCCACCAC
 781 CGTCTGCATC TTTGGAGGAC ACATACAGAT TTGTCACTTC TACTGCTATA ACTTGTCAAA
 841 AAAACACACC ACCTAAAGGA AAGGAAGATC CTTTAAAGGA CTATATGTTT TGGGAGGTGG
 901 ATTTAAAAGA AAAGTTTTCT GCAGATTTAG ATCAGTTTCC TTTAGGTAGG AAGTTTTTGT
 961 TACAGGCAGG GCTACAGGCT GCCAAACTAA AACGCCCTGC ATCATCGGCC CCACGTACCT
1021 CCACAAAGAA GAAAAAGGTT AAAAGGTAAC CATTGTCTGT TGGGTAATTG TCTGTGTCAT
1081 GTATGTGTTG TGTATGTCAA ACACAGGTTA AAAGGTAACC ATTGTTTGTT ATGTAATTGT
1141 TTTGTGTGTG TACTGTGTTG TTTGCATGTT ATGTATGTGT GTGCATGTTT GTTGTATTTG
1201 TCAGTTCCTG TATGTATGTT TTGTGTATGT ATTAATAAAG TACTGTATTT ACTAAACTAT
1261 TTATAGTAGT CTTATGTTAT GGTTGCACCC ACATGAGTAA CAATACAGTT GCTCCTAATC
1321 TATTGCATCT CCTGCCCTAC CCTGTGTCCC CTGCCCTACC CTGTGTCCTA CTTTGTTACA
1381 CTACTAATTA GCCTTATACT CTCCATTTTG TACCATTTTG TACTATCCAC CATTTTAAAT
1441 CCTAACCGAA TTCGGTTGGT CTTGGTCTTG GCACAACTTT GGTTGTCCTT GGCACAGTAA
1501 CAACTATTTT TATATAAGTT TCAGCAAACT GCTTAATCCT TTGGTTTCCT GCAGTCCCAC
1561 TGGTCTACAC TTGTTGTCCC GCCTAAACTG ACTTCTTGCT GACTCACAGG TCCTGCAGTG
1621 CAGCTAAACA ATACATTGCC TAACATTGCA TGTTTTAAAC TGCTTTTAGG CACATATTTT
1681 ATTTAAACTT TCAATGCACT AATTACAGTG TTGGCTTACA CAAGTACATC CTACGCCAAA
1741 TATGTCTTGT AAAACATGAT TAAATACTGT TACTCACCAG GTGTGCACTA CACGACCGGT
1801 TACGGTTACC GTACCCACAA CCACTTTTTT TTATAATTAT AAATTATAAT CTTATACTAG
1861 TAAAAAATAG GGTGTAACGA AAACGGTCAG ACGAAACCGG TGTATATATA TAGAACACAG
1921 TGTATAACGC ACGGCCATGT TTGAGGATCC
```

FIG. 1

HUMAN PAPILLOMAVIRUS TYPE 52 DNA SEQUENCES AND METHODS FOR EMPLOYING THE SAME

This a continuation of application Ser. No. 07/972,355, filed Nov. 5, 1992, now abandoned, which is a continuation of application Ser. No. 07/262,597, filed Oct. 26, 1988, now abandoned.

The research underlining this patent application was supported in part by National Institutes of Health Grant CA32638; the Government has certain rights in this invention.

FIELD OF THE INVENTION

The present invention relates to nucleic acid hybridization probes for human papillomavirus and particularly for human papillomavirus type 52 (hereinafter "HPV 52"); and methods for employing the same.

BACKGROUND OF THE INVENTION

A. Human Papillomavirus Types

Human papillomaviruses (hereinafter "HPV") are recognized as a cause of various epithelial lesions such as warts, condylomas and dysplasias (see *DNA Tumor Viruses*, Part 2, J. Tooze, ed., 2nd Edition, 1981, Cold Spring Harbor Laboratory, pp. 371–382d; Gissmann, L., *Cancer Surv.* 3:161 (1984); Pfister, H., *Rev. Physiol. Biochem. Pharmacol.* 99:111 (1984); Durst, M., et al., *Proc. Natl. Acad. Sci.*, USA 80:3812 (1983) and Boshart, M., et al. *EMBO J.* 3:1151 (1984)). Dysplasias of the cervix (also known as cervical intraepithelial neoplasia (CIN)) are believed to be early events in the progression to cervical cancer; the progression proceeding from mild dysplasia (CIN I), to moderate dysplasia (CIN II), to severe dysplasia, to carcinoma in situ (collectively CIN III), to invasive cancer.

Studies examining the association of HPV type with dysplasias of the cervix and cancer of the cervix have shown that HPV types 6, 11, 16, 18, 31 and 33 are associated with a high percentage of genital lesions (see Gissman, L., *Cancer Surv.* 3:161 (1984); Pfister, H., *Rev. Physiol. Biochem. Pharmacol.* 99:111 (1984); Durst, M., et al., *Proc. Natl. Acad. Sci.*, USA 80:3812 (1983); Boshart, M., et al., *EMBO J.* 3:1151 (1984); de Villiers, E.-M., et al., *J. Virol.* 40:932 (1981); Gissman, L., et al., *J. Virol.* 44:393 (1982); Lorincz, A. T., et al., *J. Virol.* 58:225 (1986) and Beaudenon, S., *Nature* 321:246 (1986)).

HPVs are grouped into types based on the similarity of their DNA sequence. Two HPVs are taxonomically classified as being of the same type if their DNAs cross-hybridize to greater than 50%, as measured by hybridization in solution under moderately stringent hybridization conditions, which are defined as approximately 25° C. below the melting temperature of a perfectly base-paired double-stranded DNA (conveniently written as $T_m-25°$ C.), followed by chromatography on hydroxyapatite to separate double-stranded DNA from single-stranded DNA (see Coggin, J. R., et al., *Cancer Res.* 39:545 (1979)). The melting temperature ($T_m$) of a perfectly base-paired double-stranded DNA can be accurately predicted using the following well-established formula:

$$T_m = 16.6 \times \log[Na^{30}] + 0.41 \times \%G{:}C + 81.5 - 0.72 \times (\%) \ (v/v) \ \text{formamide}$$

The above formula provides a convenient means to set a reference point for determining non-stringent and stringent hybridization conditions for various DNAs in solutions having varying salt and formamide concentrations without the need for empirically measuring the $T_m$ for each individual DNA in each hybridization condition.

If less than 50% of the respective HPV DNAs are able to cross-hybridize in solution under moderately stringent conditions to form fully or partially double-stranded structures, as measured and defined by the ability to bind to hydroxyapatite, then the HPV DNAs are not sufficiently related to be taxonomically classified as being of the same type. A cut-off of 50% cross-hybridization using this method is employed as the consensus criterion for the assignment of novel HPV types for nomenclature purposes. This method for measuring the degree of cross-hybridization between HPV DNAs has been historically adopted as the method to be used to determine whether two HPV DNAs represent different isolates of a common type or represent isolates of different types. The use of this criterion pre-dates the establishment of clinical criterion for determining and defining HPV types. As discussed in more detail below, the clinical criterion for determining and defining HPV types is based upon the epidemiological distribution of HPV types among genital lesions.

The above-described method of measuring the degree of cross-hybridization is based on an assessment of the extent of formation of fully or partially double-stranded DNA molecules after the hybridization reaction. However, it should be noted that conversion of 50% of the DNAs into fully or partially double-stranded DNA molecules does not imply that the nucleotide sequences of the DNAs are 50% homologous.

As discussed above, HPVs can also be grouped into types based on clinical criterion. That is, it has been observed that HPV of different types, as defined by the degree of cross-hybridization criterion described above, show distinct epidemiological distributions among genital lesions of different severities and among different geographic populations. For example, HPV 6 and HPV 11 are principally associated with benign lesions such as exophytic condylomas and to a lesser extent with flat condylomas (see Gissmann, L., et al., *Proc. Natl. Acad. Sci.*, USA 80:560 (1983)). HPV 6 and HPV 11 are also detected in certain rare types of malignant epithelial tumors (see Zachow, K. R., et al., *Nature* 300:771 (1982) and Rando, R. E., *J. Virol.* 57:353 (1986)). In contrast, HPV 16, HPV 18, HPV 31 and HPV 33 are detected with varying degrees of frequency in cervical and other anogenital cancers as well as their precursor lesions (see Durst, M., et al., *Proc. Natl. Acad. Sci.*, USA 80:3812 (1983); Boshart, M., et al., *EMBO J* 3:1151 (1984); Lorincz, A. T., et al., *J. Virol* 58:225 (1986); and Beaudenon, S., *Nature* 321:246 (1986)). This distribution of HPV 16, HPV 18, HPV 31 and HPV 33 is believed to reflect a greater risk of, or a more rapid progression to, cervical cancer arising from genital lesions infected with HPV 16, HPV 18, HPV 31 and HPV 33 as compared to lesions infected with HPV 6 and HPV 11.

HPV Types 6, 11, 16, 18 and 31 were detected in approximately 56% of 93 dysplasias and malignant cervical lesions in a series of biopsies from the United States. The remaining 44% of the lesions contained either vital sequences that could be detected only by relaxed hybridization conditions (50%) or failed to show the presence of HPV DNA. Of the HPV positive samples detected by relaxed hybridization conditions, 56% have been shown to contain either HPV 33, 35, 42, 43, 44 or 45. In addition, HPV 16 is more prevalent in Europe than in Africa (Durst, M., et al., *Proc. Natl. Acad. Sci.*, USA 80:3812 (1983)), whereas HPV 18 is more prevalent in Africa than in Europe (Boshart, M., et al., *EMBO J.* 3:1151 (1984)).

As a result, the determination of HPV types has clinical-diagnostic value and is an important factor in the assessment of risk of cancer development in patients who exhibit evidence of HPV infection. Based on the assessed risk of cancer development, appropriate therapeutic treatments can be selected.

B. Cloning of HPV Types

Recombinant DNA cloning techniques have made it possible to isolate and purify the DNA of many HPV types such as HPV types 6, 11, 16, 18, 31 and 33 (see Durst, M., et al., *Proc. Natl. Acad. Sci.*, USA 80:3812 (1983); Boshart, M., et al., *EMBO J.* 3:1151 (1984); de Villiers, E.-M., .et al., *J. Virol.* 40:932 (1981); Gissmann, L., et al., *J. Virol.* 44:393 (1982); Lorincz, A. T., et al:, *J. Virol.* 58:225 (1986); and Beaudenon, S., *Nature* 321:246 (1986)). Most of the knowledge regarding HPVs has been derived from the study of the DNA sequence in such recombinant DNAs and the use of these DNAs to prepare nucleic acid hybridization probes for detection of HPV in tissue samples.

C. Hybridization Probes

As discussed above, HPV DNA has been employed as a hybridization probe to differentiate HPV types. Two HPV DNAs of different types can be readily distinguished by hybridization under stringent hybridization conditions, which are defined as approximately 10° C. below the melting temperature of a perfectly based-paired double-stranded DNA hybrid (conveniently written as $T_m-10°$ C.), using such hybridization probes. Similarly, an HPV DNA of one type can be readily distinguished from an HPV RNA of another type by hybridization under stringent hybridization conditions which are defined as approximately 10° C. below the melting temperature of a perfectly based-paired double-stranded DNA-RNA hybrid (conveniently written as $T_m-10°$ C.), using such hybridization probes. Further, two HPV RNAs of different types can be readily distinguished by hybridization under stringent hybridization conditions, which are defined as approximately 10° C. below the melting temperature of a perfectly based-paired double-stranded RNA-RNA hybrid (conveniently written as $T_m-10°$ C.), using such hybridization probes. It should be noted that HPV DNAs or RNAs which are designated as different types using the above criterion, may in fact have as much as 80% of their nucleotide sequences in common.

Furthermore, two HPV DNAs of different types are able to cross-hybridize under non-stringent hybridization conditions, which are defined as approximately 35° C. or more below the melting temperature of a perfectly base-paired double-stranded DNA-DNA hybrid (conveniently written as $T_m-35°$ C. or more), using such hybridization probes. Similarly, an HPV DNA of one type is able to cross-hybridize with an HPV RNA of another type by hybridization under non-stringent hybridization conditions which are defined as approximately 35° C. or more below the melting temperature of a perfectly base-paired double-stranded DNA-RNA hybrid (conveniently written as $T_m-35°$ C. or more), using such hybridization probes. Further, two HPV RNAs of different types are able to cross-hybridize under non-stringent hybridization conditions, which are defined as approximately 35° C. or more below the melting temperature of a perfectly based-paired double-stranded RNA-RNA hybrid (conveniently written as $T_m-35°$ C. or more), using such hybridization probes (see Anderson, L. M., *Nucleic Acid Hybridization*, pages 73–111, eds. B. D. Hames and S. J. Higgins, I. R. L. Press, Oxford, England, and Washington, D.C., USA (1985)).

The melting temperatures of DNA-DNA, DNA-RNA and RNA-RNA hybrids of the same nucleotide sequences may be different in various chemical environments. The effect of various compounds on the relative melting temperatures of these various hybrids has been studied for several agents. For example, it is well known that increasing the concentration of formamide differentially destabilizes DNA-DNA hybrids more than DNA-RNA hybrids so that at high concentrations of formamide, such as 80% (v/v), a DNA-RNA hybrid may have a significantly higher melting temperature than a DNA-DNA hybrid of the same nucleotide sequence. As discussed above, the melting temperature of a DNA-DNA hybrid can be predicted as described in Anderson, L. M., et al., *Nucleic Acid Hybridization*, pages 73–111, eds. B. D. Hames and S. J. Higgins, I. R. L. Press, Oxford, England, and Washington, D.C., USA (1985)). Further, the melting temperature of a DNA-DNA hybrid can be empirically determined as described in Howley, P. et al., *J. Biol. Chem.* 254:4876 (1979). The melting temperature of a DNA-RNA hybrid and a RNA-RNA hybrid can also be determined by means well known in the art.

Thus, it is possible to test a tissue sample for the presence of HPV DNA or RNA in general and/or a particular HPV DNA or RNA type by nucleic acid hybridization depending upon what conditions, i.e., stringent or non-stringent, are employed for hybridization.

SUMMARY OF THE INVENTION

It has been found in the present invention that there is a new type of HPV, designated HPV52, which may play a role in cervical cancer development.

Accordingly, an object of the present invention is to provide nucleic acid hybridization probes which are specific for HPV type 52.

Still another object of the present invention is to provide a method for detecting HPV DNA or RNA in general and HPV type 52 DNA or RNA in particular, in an unknown sample of DNA or RNA, particularly an unknown sample of DNA or RNA derived from a genital lesion so as to determine the risk of cervical cancer development.

These and other objects of the present invention will be apparent from the detailed description of the invention provided hereinafter.

Thus, in one embodiment, the above-described objects of the present invention have been met by a recombinant DNA of HPV 52 comprising a cloning vector and substantially all of HPV 52 DNA or fragments thereof.

In other embodiments, the above-described objects of the present invention have been met by essentially pure HPV 52 DNA or fragments thereof or HPV 52 RNA or fragments thereof, or mixtures thereof, and by nucleic acid hybridization probes for HPV DNA or RNA in general and HPV 52 DNA or RNA in particular which have been labeled with a detectable marker.

In still another embodiment, the above-described objects of the present invention have been met by a method for detecting HPV DNA or RNA comprising:

(1) carrying out hybridization, under non-stringent conditions, with
  (a) a member selected from the group consisting of
    (i) HPV 52 DNA or fragments thereof labeled with a marker, and
    (ii) HPV 52 RNA or fragments thereof labeled with a marker;
  (b) an unknown sample of DNA or RNA; and
(2) assaying for the presence of cross-hybridization so as to detect HPV DNA or RNA in said sample.

In a further embodiment, the above-described objects of the present invention have been met by a method for detecting HPV 52 DNA or RNA comprising:

(1) carrying out hybridization, under stringent conditions, with
   (a) a member selected from the group consisting of
      (i) HPV 52 DNA or fragments thereof labeled with a marker, and
      (ii) HPV 52 RNA or fragments thereof labeled with a marker;
   (b) an unknown sample of DNA or RNA, and
(2) assaying for the presence of cross-hybridization so as to detect HPV 52 DNA or RNA in said sample.

BRIEF DESCRIPTION OF THE DRAWINGS

FIG. 1 illustrates the 1950 base nucleotide sequence of pCD15, from the middle of the L1 open reading frame through the noncoding region.

DETAILED DESCRIPTION OF THE INVENTION

Figure 2:
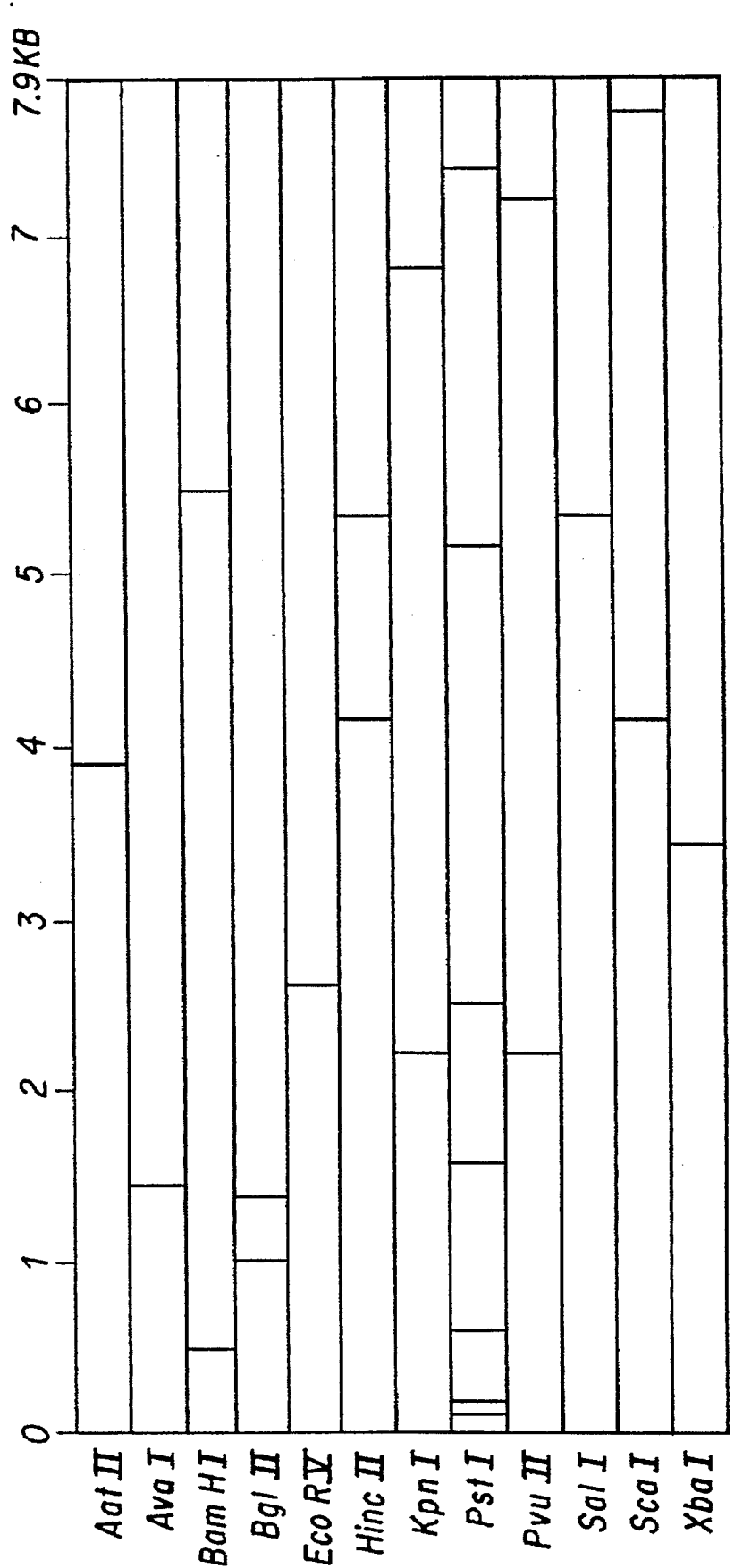
FIG. 2 graphically illustrates the restriction enzyme cleavage pattern for HPV 52.

A previously unknown HPV type has been found in the present invention, and designated HPV 52. HPV 52 has been cloned for the first time in the present invention, thus enabling the preparation of nucleic acid hybridization probes for the detection of HPV DNA or RNA in general and HPV 52 DNA or RNA in particular in an unknown sample of DNA or RNA, particularly an unknown sample of DNA or RNA derived from genital lesions.

HPV 52 was isolated and cloned from the combined DNA of biopsies of two mild dysplasias obtained from the Washington, D.C. area.

The specific cloning vector employed in the example provided herein to initially clone HPV 52 was λ L47. The plaques positive by nonstringent hybridization with HPV-16 probes from $10^5$ plaques were screened by Southern blot analysis. Three plaques contained the same DNA as determined by restriction enzyme analysis. One isolate was cloned into pUC and was designated pCD15. Messing, J., (1983), *Meth. Enzymol.* 101C:20–78. Clone pCD15 was deposited with the American Type Culture Collection 12301 Parklawn Drive, Rockville, Md. on Jun. 24, 1991, under Accession Number 75041.

HPV 52 DNA in its entirety can be excised from clone pCD15 using EcoRI restriction endonuclease and subcloned in any procaryotic and eucaryotic cloning vectors. The particular cloning vector employed for subcloning HPV 52 is not critical and can be any known procaryotic cloning vector such as pUC11, λ derived vectors such as λ charon or M13 derived bacteriophages (see Maniatis, T., et al., *Molecular Biology: A Laboratory Manual*, Cold Spring Harbor Laboratory, Cold Spring Harbor, N.Y. (1982) and Loenen, W. A. M., et al., *Gene* 20:249 (1980)) or any known eucaryotic cloning vector such as pZIP-Neo SV [X1] or pBKTK-1 (see Poueels, P. H., et al., *Cloning Vectors: A Laboratory Manual*, Elseiver, Amsterdam (1985)).

Fragments of HPV 52 DNA can similarly be excised from HPV 52 clone pCD15 using other well-known restriction endonucleases and cloned in the above-described cloning vectors.

The cloning of HPV 52 DNA or fragments thereof allows for the relatively simple production of large amounts of HPV 52 DNA or fragments thereof for use in the preparation of nucleic acid hybridization probes for HPV DNA or RNA in general and HPV 52 DNA or RNA in particular.

Hybridization of two HPV RNA strands is similar to that of two HPV DNA strands and occurs when two strands of HPV RNA are complementary to each other; that is, when a sense strand of HPV RNA hybridizes with an anti-sense strand of HPV RNA. Therefore, the term "HPV RNA" is meant to include both the sense and the anti-sense HPV RNA sequence. HPV sense strand RNA is an HPV RNA sequence which is found in HPV RNA that has been transcribed from HPV DNA. By HPV anti-sense strand RNA is meant a RNA complementary to HPV sense RNA strand which can pair and form double-stranded RNA with sense strand RNA. Sense strand RNA may include coding and non-coding regions such as a 5' and a 3' non-translated sequence. Anti-sense HPV RNA includes the complement of any sequence present on the HPV RNA sense strand.

HPV 52 DNA or fragments thereof can be subcloned in other well-known cloning vectors to take advantage of special properties of particular cloning vectors which facilitate the synthesis, in vitro, of RNA homologous to the HPV 52 DNA inserted into the cloning vector (see Maniatis, T., et al., *Molecular Biology: A Laboratory Manual*, Cold Spring Harbor Laboratory, Cold Spring Harbor, N.Y. (1982)). Examples of these cloning vectors include pT712 and pT713, each of which is commercially available from GIBCO/BRL, Gaithersburg, Md. HPV 52 DNA or fragments thereof can be subcloned into these cloning vectors so that the HPV 52 DNA or fragments thereof can serve as an efficient template for phage encoded RNA polymerases, e.g., T7, T3 or SP6. Using such cloning vectors and such RNA polymerases, HPV 52 RNA complementary to either one of the strands of HPV 52 DNA or fragments thereof can be synthesized by in vitro transcription using methods well known in the art.

The specific bacterial or eucaryotic hosts for growing the cloning vectors containing HPV 52 DNA or fragments thereof will depend upon the cloning vector employed. For example, a typical host for growing HPV 52 DNA in λ L47 includes *E. coli* NM538 (Frischanf, A. M., et al., *J. Mol. Biol.* 170:827 (1983)). Other hosts such as *E. coli* HB101 (Boyer, H. W., et al., *J. Mol. Biol.* 41:459 (1969)) can be employed when using pBR322 or pUC11 as the cloning vector. A typical host for growing HPV 52 DNA cloned in pZIP-Neo SV [X1] is Monkey Cos cells while a typical host for growing HPV 52 DNA cloned in pBKTK-1 would be any of a number of well-known mammalian cell lines (see Poueels, P. H., et al., *Cloning Vectors: A Laboratory Manual*, Elseiver, Amsterdam (1985)).

Essentially purified HPV 52 DNA or RNA or fragments thereof may also be permanently incorporated into the germ line or into somatic cells of higher organisms which are not normally susceptible to HPV infection to create a transgenic species (see Jaenisch, R., *Science* 240:1468–1474 (1988)).

By higher organism or multicellular organism is meant any multicellular animal or plant including yeast. HPV 52 DNA or RNA or fragments thereof can be inserted into the chromosomal DNA of the cells of multicellular organisms by direct injection into the pronucleus of germ line cells or by retrovirus infection or by the use of a retroviral vector, Ti plasmid vector (for plants) or embryonic stem cells. The transgenic species so created is useful for the study of the pathogenesis of HPV-induced diseases or as a reservoir for the production of HPV-specific components such as DNA, RNA or protein. Jaenisch, supra, and Varmus, H., *Science* 240:1427–1435 (1988). Botstein, D., et al., *Science* 240:1439–1443 (1988).

The hybridization of the probes of the present invention to HPV DNA or RNA in general or to HPV 52 DNA or RNA in particular will depend upon the hybridization conditions employed. That is, under non-stringent hybridization conditions, HPV 52 DNA or fragments thereof or HPV 52 RNA or fragments thereof can be employed as hybridization probes for HPV DNA or RNA in general. On the other hand, under stringent hybridization conditions, HPV 52 DNA or fragments thereof can be employed as hybridization probes for HPV 52 DNA or RNA in particular.

As discussed above, the DNAs and RNAs of different types of HPV are able to cross-hybridize under non-stringent hybridization conditions, i.e., approximately 35° C. or more below the melting temperature of a perfectly base-paired double-stranded DNA having a base composition equal to that of HPV DNAs or RNAs as a general group.

Thus, it is possible to test an unknown sample of DNA or RNA for the presence of HPV by carrying out hybridization under non-stringent hybridization conditions, i.e., approximately 35° C. below the melting temperature of a perfectly base-paired double-stranded DNA having a base composition equal to that of HPV DNAs or RNAs as a general group.

Furthermore, it is possible to test an unknown sample of DNA or RNA for the presence of a particular HPV type and to identify that type by carrying out hybridization under stringent hybridization conditions, i.e., approximately 10° C. below the melting temperature of a perfectly base-paired double-stranded DNA having a base composition equal to that of HPV DNAs or RNAs as a general group.

In the methods of the present invention, hybridization under non-stringent conditions is carried out by first hybridizing under non-stringent hybridization conditions followed by washing under non-stringent hybridization conditions.

In addition, in the methods of the present invention, hybridization under stringent conditions is carried out by either first hybridizing under non-stringent hybridization conditions followed by washing under stringent hybridization conditions or by first hybridizing under stringent hybridization conditions followed by washing under stringent hybridization conditions. In the first method, i.e., first hybridizing under non-stringent hybridization conditions followed by washing under stringent hybridization conditions, hybrids which form between DNAs or RNAs of different types are unstable but hybrids which form between DNAs and RNAs of the same type are stable.

To determine if an unknown sample of DNA or RNA is of the same or different HPV type as the hybridization probe employed, hybridization is preferably carried out under non-stringent hybridization conditions followed by washing under non-stringent hybridization conditions. After assaying for the presence of hybrids, the detected hybrids are washed under stringent hybridization conditions. In this method, the amount of hybrids which remains after hybridizing under non-stringent hybridization conditions is determined and compared with the amount of hybrids present after washing under stringent hybridization conditions. If the washing under stringent hybridization conditions results in no or minimal reduction in the amount of hybrids formed, then this indicates that the hybrids originally formed, i.e., the ones which formed under non-stringent conditions, were between DNAs or RNAs of the same type. Conversely, abolition of hybrids or a severe reduction of the amount of hybrids which remain after washing under stringent hybridization conditions indicates that the hybrids originally formed, i.e., ones which formed under non-stringent hybridization conditions, were between DNAs or RNAs of different types.

Accordingly, within the context of the present invention, two HPVs are considered to be of the same type if they meet the criterion for the degree of cross-hybridization discussed above.

The ability of the HPV DNA or RNA to bind to the unknown sample of DNA or RNA under stringent hybridization conditions is indicative of a high degree of nucleotide sequence homology. On the other hand, the ability of the HPV DNA or RNA to bind to the unknown sample of DNA or RNA only under non-stringent hybridization conditions is indicative of a low or intermediate degree of nucleotide sequence homology. The exact degree of nucleotide sequence homology can only be determined by directly sequencing the unknown DNA and comparing that with the known sequence of the HPV DNA.

In situations in which the detection of HPV DNA or RNA in general in an unknown sample of DNA or RNA, for example in an unknown sample of DNA or RNA derived from a genital lesion, is being carried out, it is, as a practical matter, advantageous to utilize a hybridization probe composition comprising a mixture of hybridization probes. These hybridization probes comprise probes with sequences representative of all or most of the types suspected of being present in the unknown sample of DNA or RNA. A hybridization probe mixture of DNA or RNA sequences representative of HPV types 6, 11, 16, 18, 31, 33 and 52 is particularly advantageous when the unknown sample of DNA or RNA is derived from a genital lesion because these HPV types are most likely to be found in genital lesions. Other known HPV types are seldom or never found in genital lesions. For example, HPV types 1, 2 and 4 are generally found in other types of lesions, i.e., cutaneous warts (see Heilman, C. A., et al., *J. Virol.* 360:395 (1980)). Thus a hybridization probe mixture of DNA or RNA sequences containing HPV types 6, 11, 16, 18, 31, 33 and 52 may be advantageous when the unknown sample of DNA or RNA is derived from genital lesions.

Examples of sequences of HPV types 6, 11, 16, 18, 31, and 33 which can be employed in the hybridization probe mixture are described in Gissmann, L., *Cancer Surv.* 3:161 (1984); Pfister, H., *Rev. Physiol. Biochem. Pharmacol.* 99:111 (1984); Durst, M., et al., *Proc. Natl. Acad. Sci.*, USA 80:3812 (1983); Boshart, M., et al., *EMBO J.* 3:1151 (1984); Lorincz, A. T., et al., *J. Virol.* 58:225 (1986); and Beaudenon, S., *Nature* 321:246 (1986). Further, examples of sequences of HPV Types 1, 2, and 4 which can be employed in the hybridization probe mixture are well known in the art (see Heilman, C. A., et al., *J. Virol.* 360:395 (1980)). Thus, with the disclosure herein as to HPV 52 and with the knowledge of one skilled in the art as to HPV types 6, 11, 16, 18, 31, and 33 and to other HPV types such as HPV Types 1, 2, and 4, hybridization probe mixtures can be readily prepared.

In the hybridization probe mixtures, the particular percentage of DNAs or RNAs of each HPV type is not critical in the present invention. Generally, roughly equal molar amounts of DNAs or RNAs of each HPV type are employed in the mixture.

Nucleic acid hybridization as a means of detecting and typing HPV can be carried out in solution as described above (see Coggins, J. R., et al., *Cancer Res.* 39:545 (1979)) or on a solid support (see Maniatis, T., et al., *Molecular Biology: A Laboratory Manual*, Cold Spring Harbor Laboratory, Cold Spring Harbor, N.Y. (1982)) or in situ (see Brigati, D. J., et al., *Virol.* 126:32 (1983) and Beckmann, A. M., et al., *J. Med. Virol.* 16:265 (1985)).

Hybridization on a solid support can be carried out using a number of different procedures. One such procedure involves immobilizing all of the unknown DNAs or RNAs on a solid support in single-stranded form, followed by hybridization with labeled HPV 52 DNA or fragments thereof or labeled HPV 52 RNA or fragments thereof.

In a preferred embodiment, the unknown samples are separately immobilized to the solid support. In another preferred embodiment, the unknown samples are mixed together before immobilization on the solid support. Mixing samples is especially advantageous for the rapid screening of large numbers of samples, the majority of which would be negative.

Alternatively, the purified unknown DNAs can be digested with one or more restriction endonucleases and the resulting DNA fragments in the samples can be separated electrophoretically. The DNA fragments can then be transferred to a solid support and hybridized with labelled HPV 52 DNA or fragments thereof or labelled HPV 52 RNA or fragments thereof.

Hybridization in situ using either isotopic or non-isotopic detection methods is performed on glass slides and the end result of the procedure is viewed through a microscope. In this procedure, the DNA or RNA is not purified from the cells but is left with all of the other cellular components. Singer, R. H., et al., *BioTechnology* 4:230–250 (1986).

HPV 52 RNA or fragments thereof are preferably used as nucleic acid hybridization probes for HPV DNA in general and HPV 52 DNA in particular when using crude extracts, particularly crude genital lesion extracts rather than purified DNA, e.g., from such genital lesions.

HPV 52 anti-sense RNA or fragments can also be used as blockers or regulators of HPV gene expression in general and HPV 52 gene expression in particular by hybridization to HPV sense strand RNA. Use of anti-sense RNA probes to block gene expression is discussed in Lichtenstein, C., *Nature* 333:801–802 (1988), incorporated herein by reference.

HPV 52 anti-sense RNA or fragments thereof can be used without labeling as a probe to block expression of HPV in general and HPV 52 in particular by exposure of the replicating virus to said probe. Exposure can occur either by any method which exposes the virus to the anti-sense RNA such as in an ointment or by incorporating a source of anti-sense RNA into the cell, for example, by transfection with a second virus, or by transformation or microinjection.

Vital genomes, because of their uniqueness and limited complexity, lend themselves especially well to varied hybridization approaches such as radiolabeling of nucleic acids used as probes, DNA-DNA and RNA-DNA hybridization with immobilized nucleic acids, cytohybridization, and methods of kinetic analysis of DNA-DNA and RNA-DNA hybridization in solution. Hybridization techniques and their application to DNA diagnostics have recently been reviewed, Landegren, U., et al., *Science* 242:229–237 (1988).

The purity of the nucleic acid used as the probe is a most critical element in specific hybridization. When it is desired to use virus as the source of the probe, it is preferred that the virus be harvested from extracellular fluids rather than from infected cells, especially where complementary RNA (cRNA) or complementary DNA (cDNA) are employed. Viruses harvested from cells carry along contaminated cellular DNA, the latter not always eliminated by DNase treatment. Thus, the first step is to procure virus which is highly purified by any method known to the art that conserves the integrity of the virions so that treatment of the lysed cells with DNase will not cause fragmentation of the encapsulated genome. The extracted viral DNA should be rigorously purified at this point, so that the genome emerging from purification is largely unfragmented and separable from cellular nucleic acids on the basis of physical properties such as size, as well as density or supercoiled state. Following this, the highly purified genome is treated with endonucleases to fragment same, followed by isolation and recovery of the fragment containing the desired nucleotide sequence coding for the type-specific or genus-specific viral protein. Alternatively, a specified polynucleotide probe can be independently synthesized either in a biological system or in a chemical reaction in vitro. Biological systems include both prokaryotic organisms like bacteria and eukaryotic organisms such as yeast, isolated cells in culture, germ line cells in multicellular organisms, somatic tissue cells in multicellular organisms or plant cells. A more complete discussion of nucleic acid hybridization technology may be found in *Nucleic Acid Hybridization*, B. D. Hames and S. J. Higgins, eds., IRL Press, Washington, D.C., 1985.

The polynucleotide or oligonucleotide probe may be labeled with an atom or inorganic radical, most commonly using radionucleotides, but also perhaps heavy metals. In some situations, it may also be possible to employ an antibody which will bind specifically to the probe hybridized to the single-stranded DNA. Oligonucleotide probe technology is disclosed by Szostak, J. W., et al., *Meth. Enzymol.* 68:419–428 (1979), incorporated by reference herein.

Most commonly, a radioactive label is employed, suitable radioactive labels including $^{32}$P, $^{3}$H, $^{14}$C, $^{35}$S, $^{125}$I, or the like. Any radioactive label may be employed which provides for an adequate signal and has sufficient half-life. Other labels include ligands, fluorescers, chemiluminescers, enzymes, antibodies, and the like.

When employing HPV 52 RNA as a hybridization probe for detecting HPV 52 DNA in an unknown sample of DNA, it is preferable that the DNA-RNA hybrids formed after first hybridizing under stringent hybridization conditions, are treated with pancreatic RNaseA (about 20 mg/ml in 50 mM NaCl (pH 7.0)) at room temperature, followed by washing under stringent hybridization conditions.

HPV 52 DNA or fragments thereof can be radioactively labeled, for example, by "nick-translation" by well-known means, as described in, for example, Rigby, P. J. W., et al., *J. Mol. Biol.* 113:237 (1977) and by T4 DNA polymerase replacement synthesis as described in, for example, Deen, K. C., et al., *Anal. Biochem.* 135:456 (1983)). Alternatively, HPV 52 DNA or fragments thereof can be synthesized and labeled or detected in a sample using oligonucleotide primers and enzymatic reactions such as the polymerase chain reaction, Marx, J. L., *Science* 140:1408–1410 (1988).

HPV 52 RNA or fragments thereof can be labelled with a radioactive marker by in vitro transcription as described in, for example, Davanloo, P., et al., *Proc. Natl. Acad. Sci.*, USA 81:2035 (1984)). Since RNA polymerases can utilize labelled precursors, it is possible to synthesize labelled RNA by this method so as to prepare HPV 52 RNA probes for the detection of HPV DNA or RNA in general or HPV 52-DNA or RNA in particular.

HPV 52 DNA or fragments thereof or HPV 52 RNA or fragments thereof are also useful as nucleic acid hybridization probes for HPV DNA or RNA in general and HPV 52 DNA or RNA in particular when labeled with a non-radioactive marker such as biotin, an enzyme or fluorescent group. Biotin acts as a hapten-like group and can be bound to the DNA or RNA and detected by binding an avidin-conjugated enzyme or streptavidin-conjugated enzyme to the biotin followed by washing to remove non-specifically bound enzyme. Upon addition of appropriate substrates for the enzyme, the conversion of the substrate to a colored product can be detected (see Leary, J. J., et al., *Proc. Natl. Acad. Sci.*, USA 80:4045 (1983)). Examples of such enzymes include alkaline phosphatase and horseradish peroxidase. Renz, M., et al., *Nuc. Acids Res.* 12:3435–3444 (1984). In addition, fluorescent molecules such as fluorescein and rhodamine can be chemically conjugated to avidin or strepdavidin and employed as the non-radioactive marker.

Alternatively, the above-described enzymes or fluorescent molecules can be chemically conjugated directly to the HPV 52 DNA or fragments thereof or HPV 52 RNA or fragments thereof as described in, for example, Renz, M., *EMBO J.* 6:817 (1983), and used in this manner as hybridization probes.

The thus labelled HPV 52 DNA or HPV 52 RNA or fragments thereof can be used as described above in hybridization studies with an unknown sample or a mixture of unknown samples of DNA or RNA, particularly an unknown sample or a mixture of unknown samples of DNA or RNA derived from a genital lesion, to determine if the sample contains HPV DNA or RNA in general and HPV 52 DNA in particular.

The unknown sample or mixture of unknown samples of DNA or RNA, in addition to being derived from a genital lesion, can be derived from other lesions such as throat, oral or skin lesions.

The unknown sample or mixture of unknown samples of DNA or RNA can be obtained by, for example, biopsying an epithelial lesion, scraping the cervix or swabbing the cervix to obtain exfoliated cells. In addition, the unknown sample or mixture of unknown samples of DNA or RNA can be obtained from bacterial cells in which DNA or RNA from a lesion has been cloned using well known means as described in Maniatis, T., et al., *Molecular Biology: A Laboratory Manual*, Cold Spring Harbor Laboratory, Cold Spring Harbor, N.Y. (1982) and Gissmann, L., *Cancer Surv.* 3:161–181 (1984).

In the methods of the present invention, assaying for cross-hybridization can be carried out by assaying for the presence of the radioactive or non-radioactive marker associated with double-stranded nucleic acid hybrids. The methods for determining whether a specific marker is present will depend upon the marker employed and are well known in the art.

In a preferred embodiment, the presence of HPV DNA and/or RNA, or HPV 52 DNA and/or RNA or fragments thereof in an unknown sample is detected utilizing specific HPV 52 oligonucleotide primers and DNA polymerase in the polymerase chain reaction as described by Marx, J. L., *Science* 140:1408–1410 (1988). Mixtures of linkers specific for different HPV types can be synthesized by techniques known to those in the art and used to detect the presence of any one of these types in the unknown sample by hybridization of the linkers under stringent conditions. Alternatively, the presence of any HPV DNA or RNA in an unknown sample can be detected by hybridizing the primers to a sample under non-stringent conditions.

In another preferred embodiment HPV DNA and/or HPV RNA, and especially HPV 52 DNA and/or HPV 52 RNA is detected using an amplifiable HPV 52 RNA sequence as a probe, for example, as used with the Q-beta-replicase system. Chu, B. C. F. et al., *Nucl. Acids Res.* 14:5591–5603 (1986).

The particular size of the HPV 52 DNA or HPV 52 RNA fragments which can be employed as hybridization probes in the present invention is not critical. The size of the HPV 52 DNA or HPV 52 RNA fragments can be, for example, from about 15 to about 8000 bases or base pairs, depending on whether single stranded or double stranded probes are employed, preferably about 300 to about 800 bases or base pairs. When carrying out hybridization in situ, it is preferable that the size of the HPV 52 DNA or HPV 52 RNA fragments is smaller than about 500 bases or base pairs since fragments of this size hybridize in situ more efficiently than HPV DNA or HPV RNA fragments of a larger size. Even smaller fragments of 15–100 bases are desirable as the primers for use with the polymerase chain reaction. When using double stranded DNA or RNA, the DNA or RNA must be denatured prior to carrying out hybridization.

The HPV 52 DNA fragments can be obtained by restriction endonuclease digestion of HPV 52 clone pCD15 or by synthetically manufacturing such using any of the commercially available DNA synthesizing apparatus or by well known chemical methods using the HPV 52 DNA sequence which can be determined by well known means (Sanger, S., et al., *Proc. Natl. Acad. Sci.*, USA 74:5363 (1977)).

The following example is given to further illustrate the present invention and is no way intended to limit the scope of the present invention. Unless otherwise indicated, all parts, percents, ratios and the like are by weight.

EXAMPLE 1

Cloning of HPV 52 DNA

The starting material employed was a cervical intraepithelial neoplasia obtained from a biopsy sample consisting of a few milligrams of tissue. Total DNA was purified as described in Maniatis, T., et al., *Molecular Biology: A Laboratory Manual*, Cold Spring Harbor Laboratory, Cold Spring Harbor, N.Y. (1982). More specifically, the tissue was minced, then digested in 1.0 ml of 50 mM Tris-HCl, pH 8.0 containing 0.6% (w/v) sodium dodecyl sulfate and 50 µg/ml proteinase K at 37° C. overnight. The resulting digest was extracted twice with 1.0 ml of phenol:chloroform (1:1 (v/v)). DNA was then precipitated from the aqueous phase by addition of 2 volumes of 90% (v/v) ethanol. The precipitated DNA was redissolved in 10 mM Tris, 1.0 mM EDTA buffer, pH 8.0 (hereinafter "TE buffer") at a concentration of about 1.0 mg/ml.

The DNA was digested to completion with Pst1, electrophoresed in 1.0% (w/v) agarose gels and DNA transferred to nitrocellulose filters as described in Southern, E. M., *J. Mol. Biol.* 98:503 (1975). The filters were then probed under non-stringent hybridization conditions ($T_m$–35° C.) and stringent hybridization conditions ($T_m$–10° C.) with DNA from HPV type 16. Hybridization was performed overnight at 43° C. in 1.0M NaCl, 50 mM sodium phosphate buffer (pH 7.4), 1.0 mM EDTA, 2% (w/v) sodium dodecyl sulfate, 0.1% (w/v) gelatin, 50 µg/ml tRNA and 30% (v/v) formamide. Four 30 minute washes were performed at 55° C. in 1.2× SSC (1× SSC is 0.15M NaCl plus 0.015M sodium citrate), 10 mM sodium phosphate (pH 7.4), 1.0 mM EDTA and 0.5% (w/v) sodium dodecyl sulfate. Hybridization was achieved under non-stringent conditions with HPV type 16, but not under stringent hybridization conditions.

The resulting purified DNA and λ L47 were digested with EcoRI restriction endonuclease, which produced a fragment of 8 kb. The fragment was cloned into the single EcoRI site of λ L47. More specifically, 2.0 µg of the resulting purified DNA, and 2.0 µg of λ L47 DNA were cut with 10 units of EcoRI in a total volume of 50 µl of TE buffer for 1 hr at 37° C. The resulting reaction mixtures were then diluted with 400 µl of the TE buffer and phenol extracted with equal volumes of phenol:chloroform as described above. The aqueous phases were then extracted with chloroform: isoamyl alcohol (24:1 (v/v)) and DNA from the aqueous phases were precipitated with 80% (v/v) ethanol and dried. The dried DNAs were then each suspended in 10 µl of 1× ligase buffer comprising 66 mM Tris-HCl, 6.6 mM $MgCl_2$, 10 mM DTT and 1.0 mM ATP and incubated at 42° C. for 2 hours to allow the λ arms to anneal. Next, 0.5 µl of T4 DNA ligase, i.e., about 1 unit, and 0.5 µl of 10 mM ATP, pH 7.0 was added to each reaction solution and ligation was allowed to proceed at 12° C. overnight.

Next, the ligation products were packaged to form infectious phage and used to infect *E. coli* L47. More specifically, a single colony of *E. coli* L47 growing on an agarose plate comprising 10 g Tryptone and 5.0 g NaCl per liter (hereinafter "TN medium") was selected and grown overnight at 37° C. in 20 ml of TN medium on a shaking platform (250 rpm) to early stationary phase. The cell culture was then diluted four fold with TN medium and grown for 3 hours. Next, the cells were harvested by centrifuging for 5 minutes at 5,000 rpm in a Sorvall NB-4 rotor and the resulting cell pellet was resuspended in 0.25 of the original volume, in 10 mM $MgSO_4$ and stored at 4° C.

The packaged infectious phages were prepared using a commercially available BRL Lambda In Vitro Packaging System (see Maniatis, T., et al., *Molecular Biology: A Laboratory Manual*, Cold Spring Harbor Laboratory, Cold Spring Harbor, N.Y. (1982)).

100 µl of an appropriate dilution of packaged phage in phage storage buffer comprising 0.5M Tris-HCl (pH 8.0), 0.1M NaCl, 0.01M $MgSO_4$ and 0.01% (w/v) gelatin (Difco) to give $1.5 \times 10^4$ plaques per 9 cm diameter plates, was added to 100 µl of *E. coli* NM538 prepared as described above in a 10–15 ml test tube, gently mixed and incubated at room temperature for 15 minutes. Then, the cell-phage solution was plated on Trypticase soy broth agar plates comprising 10 g of Trypticase soy broth, 5.0 g NaCl and 15 g agar per liter, which had been prepared at least one day in advance and which had been prewarmed at 37° C. Thereafter, 3–5 ml of an agarose overlayer comprising 0.5% agarose (ultrapure, electrophoresis grade) dissolved in 10 mM $MgSO_4$, which had been heated in a microwave oven until the solution boiled and then cooled to 45° C. before use, was placed over the plated cells-phage. After the agarose had solidified, the plates were transferred to a 37° C. forced-air incubator with good circulation with the lids of the plates cracked for 30 minutes and then the lids were closed and the plates inverted. After 8–12 hours, plaques became apparent.

Infection resulted in confluent lysis of bacteria on the plates. Recombinant phage carrying HPV DNA were localized by performing "plaque lifts" as described by Benton, W. D., et al., *Science* 196:180 (1977). More specifically, confluent lysed plates were placed at 4° C. for 1 hour to harden the agarose. Then, an appropriately sized piece of nitrocellulose filter was placed onto each plate by bowing it in the middle, touching the center of the plate and working the contact points toward the edge. Then, four asymmetric holes were punched through the nitrocellulose filter and the agar with a small gauge needle and the positions of the holes were marked on the bottom of the plate with a permanent marker. This allowed the nitrocellulose filter and any other areas containing positive signals to be referenced to corresponding positions on the plates. After 10 minutes, the nitrocellulose filters were removed and the DNA was denatured by placing the nitrocellulose filters, plaque side facing upwards, into a dish containing 200 ml of 0.5M NaOH, 2.0M NaCl for 1 minute. The nitrocellulose filters were then neutralized by immersion in 500 ml of 0.5M Tris-HCl, 2.0M NaCl, pH 7.5 for 5 minutes. Next, the filters were rinsed in 6× SSC comprising 0.9M NaCl, 0.09M sodium citrate for 1 minute, dried on Whatman 3 MM paper and then baked for 30 minutes at 80° C. under vacuum.

Thereafter, non-stringent hybridization using HPV 16 DNA labelled with $^{32}P$ by "nick translation" as a probe was carried out on the DNA isolated from the lifted plaques (see Rigby, P. J. W., et al., *J. Mol. Biol.* 113:237 (1977) and Maniatis, T., et al., *Molecular Biology: A Laboratory Manual*, Cold Spring Harbor Laboratory, Cold Spring Harbor, N.Y. (1982)) followed by washing and autoradiography. More specifically, hybridization was performed at 41° C. in a solution comprising 1.0M NaCl, 28% (v/v) formamide, 50 mM N-Tris (hydroxymethyl)-methyl-2-aminoethane sulfonic acid (hereinafter "TES"), 10× Denhardt solution, 0.1 mM EDTA and 10 mM sodium phosphate (pH 7.4). Then a non-stringent wash was carried out at 52° C. using 1.1× SSC (comprising 0.165M NaCl and 0.0165M sodium citrate) in 10 mM sodium phosphate (pH 7.4), 0.1 mM EDTA.

By correspondence with the sites of radioactive exposure, a region of the plate containing phage, which contained DNA that hybridized to HPV 16 DNA, was excised and used to reinfect *E. coli* as described above. Localization of phage plaques containing HPV DNA was accomplished by repeating the above procedure. One plaque was identified from among the $10^5$ plaques screened from the cloning using the EcoRI digested DNA. The cloned fragment exhibited a size of 8 kb and was designated clone CD15. One plaque was identified from among the $10^5$ plaques screened from the cloning using the EcoRI digested DNA. The cloned fragment exhibited a size of 8 kb and was designated clone CD15.

The HPV DNA of HPV 52 clone CD15 was then digested with EcoRI and subcloned in the single EcoRI site of pUC. The resulting recombinant DNA was designated HPV 52 clone pCD15.

EXAMPLE 2

Characterization of HPV 52 DNA

1. Hybridization Studies

Hybridization studies were carried out on HPV 52 clone pCD15 DNA to demonstrate that HPV 52 clone pCD15 was a new HPV type.

More specifically, $^{32}P$ "nick translated" DNA prepared from HPV 52 clone pCD15 was hybridized by Southern blotting under stringent conditions to 5 ng of DNA from HPV types 1 to 51. DNA from HPV types 1 to 42 were obtained from Dr. Gerard Orth of the Institut Pasteur, Paris, France, the assignor of HPV type designations, Dr. Ethel-Michelle de Villiers of the Papilloma Reference Center in Heidelberg, West Germany, and Life Technologies, Inc., in pre-immobilized form on nitrocellulose filters. More specifically, hybridization was performed at 41° C. in a solution comprising 1.0M NaCl, 28% (v/v) formamide, 50 mM N-Tris TES, 10× Denhardt solution, 0.5 mM EDTA, and 20 mM sodium phosphate (pH 7.4). Then, a stringent wash was carried out at 65° C. using 0.03× SSC (comprising 0.0045M NaCl and 0.00045M sodium citrate) in 10 mM sodium phosphate (pH 7.4), 0.1 mM EDTA.

At standard hybridization conditions ($T_m$–25° C.), saturation hybridization and hydroxyapatite chromatography showed pCD15 and HPV 33 to have 28% DNA sequence homology. Since type designations are based on 50% or less DNA sequence homology under standard conditions of hybridization, this isolate represents a new HPV.

While significant homology was detected between the recombinant DNA of HPV 52 clones pCD15 and HPV 33 and most of the other HPV types under non-stringent hybridization conditions, no homology was observed with any of HPV types 1–51 under stringent hybridization conditions, thus demonstrating that HPV 52 clone pCD15 represents a new HPV type.

2. Nucleotide Sequence

The partial nucleotide sequence from the middle of the L1 open reading frame through the noncoding region for HPV 52 clone pCD15 is shown in FIG. 1.

3. Restriction Enzyme Cleavage Map

The restriction enzyme cleavage map for HPV 52 is shown in FIG. 2. The following restriction enzymes do not cut HPV 52 DNA: BanII, BclI, HpaI, HindIII, SacI, SphII, SphI, XhoI.

4. Genomic Organization

Figure 3:
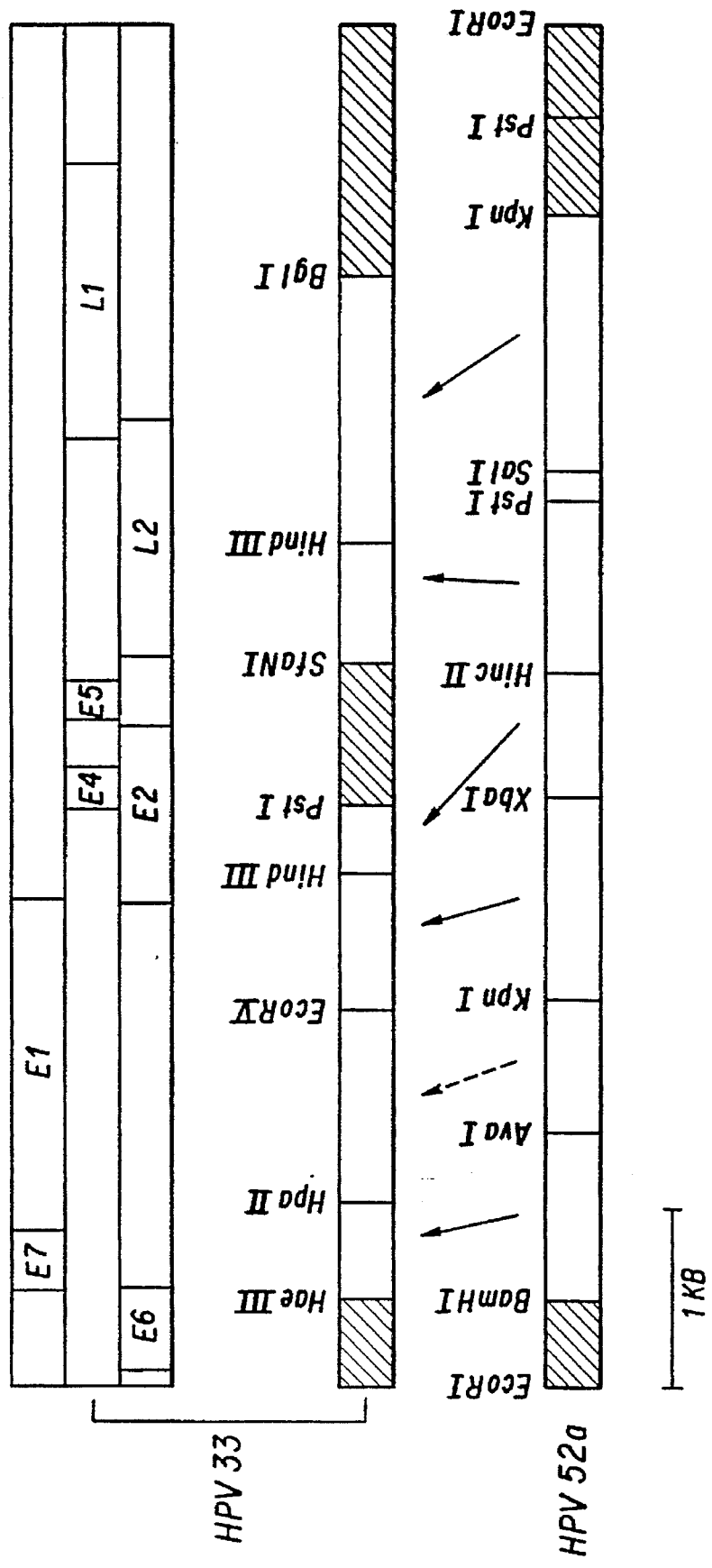
FIG. 3 shows regions of partial homology between HPV 33 and HPV 52 DNA as determined by nucleic acid hybridization under non-stringent hybridization conditions. The arrows connect regions which exhibit homology. The positions of the open reading frames deduced for HPV 33 are shown above the homology map. The shaded blocks indicate regions of little or no homology. The solid arrows connect regions of strong homology. The dashed arrows connect regions of weak homology.

In order to demonstrate that the genome of HPV 52 had the same or similar open reading frame organization to HPV 33, the following hybridization studies were carried out. Purified DNA from HPV 52 clone pCD15 was subjected to Southern blotting using $^{32}$P "nick translated" fragments of HPV 33 DNA as a probe under non-stringent conditions and under stringent conditions as described above. These fragments were hybridized to Southern blots of HPV 33 digested with a variety of restriction enzymes. Most of the fragments of HPV 52 hybridized to discrete fragments of HPV 33 (FIG. 3). Five of the six HPV 52 cross-hybridizing fragments formed stable duplexes with HPV 33 fragments at $T_m$–10; the remaining fragment only hybridized at $T_m$–30 with HPV 33. Based on these results, the HPV 52 genome appears to be collinear with the HPV 33 genome. HPV 52 restriction fragments failed to cross-hybridize with two regions of the HPV 33 genome. One region encompassed the 3' end of the early region and the other extended from the 3' end of the L1 open reading frame (ORF) into the E6 ORF.

Figure 4:
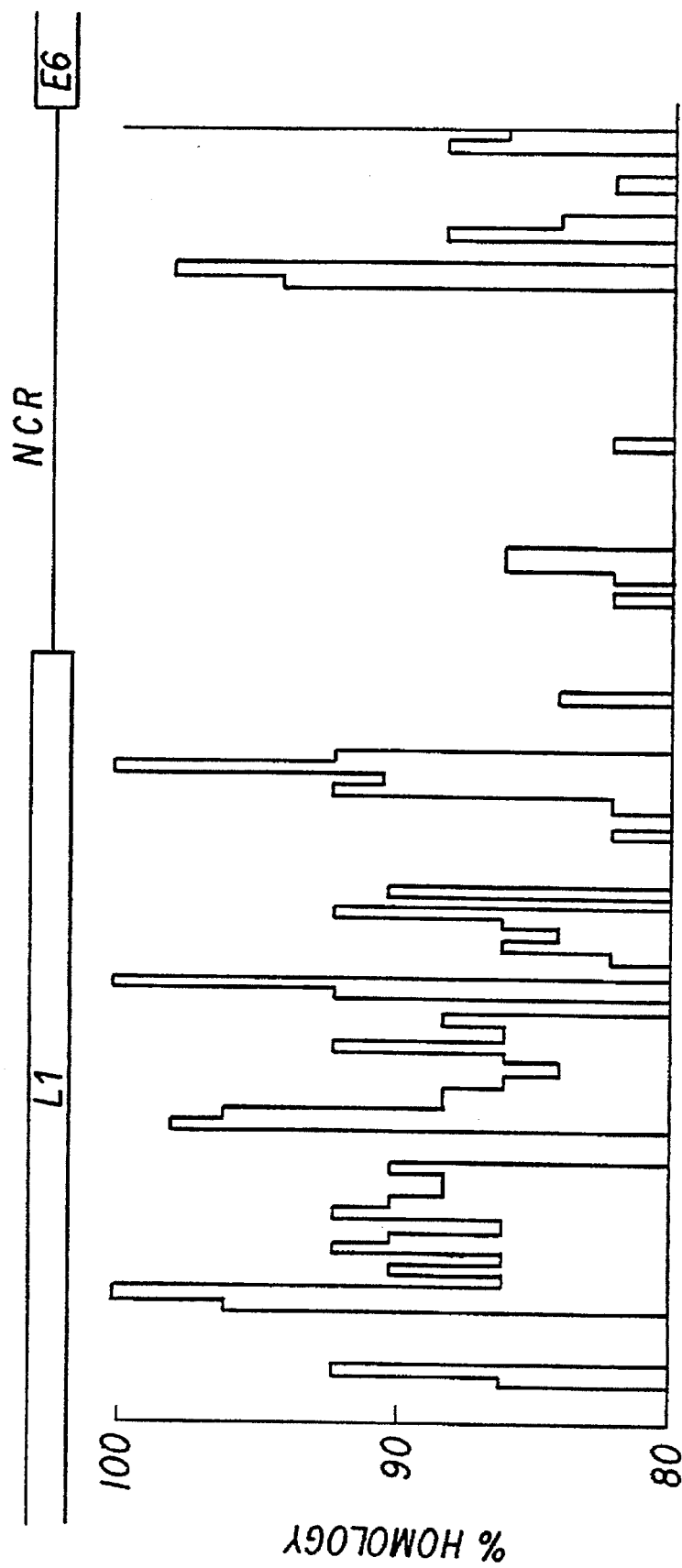
FIG. 4 graphically illustrates a comparison of the sequence homology of the L1 open reading frame and noncoding region, of HPV 52 and HPV 33.

To analyze these nonhomologous regions further, we sequenced 1,950 nucleotides from a point 346 nucleotides 5' to the unique KpnI site on the HPV 52 genome through the 5' BamHI site (see FIG. 1). This region would be equivalent from amino acid 153 of the L1 ORF through the noncoding region of HPV 33. Comparison of the nucleotide sequence of HPV 33 and HPV 52 revealed 75% sequence homology in the L1 ORF and less than 50% homology in the noncoding region. This abrupt change in homology between the L1 ORF and noncoding region is shown in FIG. 4. Comparison of the amino acid sequence of the partial nucleotide sequence of the L1 ORF revealed 82% amino acid homology between these two viruses.

EXAMPLE 3

Prevalence Studies

Prevalence studies indicated that HPV52 sequences were present in 3 of 137 (2%) of cervical intraepithelial neoplasia and in 1 of 48 (2%) of cervical squamous cell cancers from the United States.

While this invention has been described in detail and with reference to specific embodiments thereof, it will be apparent to one skilled in the art that various changes and modifications could be made therein without departing from the spirit and scope thereof.

I claim:

1. A recombinant DNA of HPV 52 comprising a cloning vector and HPV 52 DNA,
   wherein the length of the HPV 52 DNA is between approximately 15 and 8000 nucleotide bases,
   wherein the HPV 52 DNA consists of all or a fragment of an HPV DNA, wherein the HPV DNA cross-hybridizes to the HPV portion of clone pCD15 to greater than 50% under moderately stringent conditions, and
   wherein the HPV 52 DNA does not hybridize to DNA from HPV types 1 through 51 under stringent conditions.

2. The recombinant DNA of HPV 52 as claimed in claim 1, wherein said cloning vector is selected from the group consisting of pBR322, pUCll, λ charon, λ L47, M13 derived bacteriophage, pZIP-Neo SV [XI], pBKTK-1, pT712 and pT713.

3. The recombinant DNA of HPV 52 as claimed in claim 1, wherein said recombinant DNA of HPV 52 contains a non-protein encoding region of HPV 52 DNA, from the region between regions L1 and E6.

4. The recombinant DNA of HPV 52 of claim 1, wherein said recombinant DNA is labelled with a detectable label.

5. The recombinant HPV 52 DNA of claim 1 wherein the HPV 52 DNA is about 300 to 800 nucleotide bases in length.

6. The recombinant DNA of claim 5, wherein the HPV 52 DNA is about 300 to 800 nucleotide bases of the HPV portion of clone pCD15.

7. The recombinant DNA of HPV 52 as claimed in claim 1, wherein the HPV DNA is the HPV portion of clone pCD15.

8. Essentially pure HPV 52 DNA, wherein the length of the HPV 52 DNA is between approximately 15 and 8000 nucleotide bases,
   wherein the HPV 52 DNA consists of all or a fragment of an HPV DNA, wherein the HPV DNA cross-hybridizes to the HPV portion of clone pCD15 to greater than 50% under moderately stringent conditions, and
   wherein the HPV 52 DNA does not hybridize to DNA from HPV types 1 through 51 under stringent conditions.

9. The essentially pure HPV 52 DNA of claim 8, wherein said DNA is about 300 to about 800 nucleotide bases in length.

10. The essentially pure HPV 52 DNA as claimed in claim 9, wherein said HPV 52 DNA is derived from the non-protein encoding region of HPV 52 DNA between regions L1 and E6.

11. The essentially pure HPV 52 DNA of claim 8, wherein said HPV 52 DNA is labelled with a detectable label.

12. The essentially pure HPV 52 DNA as claimed in claim 8, wherein the HPV DNA is the HPV portion of clone pCD15.

13. Essentially pure HPV 52 RNA, wherein the length of the HPV 52 RNA is between approximately 15 and 8000 nucleotide bases, wherein the HPV 52 RNA consists of all or a fragment of an HPV RNA, wherein the HPV RNA cross-hybridizes to the HPV portion of clone pCD15 to greater than 50% under moderately stringent conditions, and wherein the HPV 52 RNA does not hybridize to DNA from HPV types 1 through 51 under stringent conditions.

14. The essentially pure HPV 52 RNA of claim 13, wherein said RNA is about 300 to about 800 nucleotide bases in length.

15. The essentially pure HPV 52 RNA as claimed in claim 13, wherein the sequence of said HPV 52 RNA is the sequence or complement of the sequence of a non-protein encoding region of HPV 52 RNA from between regions L1 and E6.

16. The essentially pure HPV 52 RNA of claim 13, wherein said HPV 52 RNA is labelled with a detectable label.

17. The essentially pure HPV 52 RNA as claimed in claim 13, wherein the HPV RNA corresponds to the HPV portion of clone pCD15.

18. An HPV 52 hybridization probe comprising a member selected from the group consisting of
 (i) HPV 52 DNA labelled with a detectable label, and
 (ii) HPV 52 RNA labelled with a detectable label,
 wherein the length of the HPV 52 DNA or HPV 52 RNA is between approximately 15 and 8000 nucleotide bases,
 wherein the HPV 52 DNA consists of all or a fragment of an HPV DNA, wherein the HPV DNA cross-hybridizes to the HPV portion of clone pCD15 to greater than 50% under moderately stringent conditions,
 wherein the HPV 52 RNA consists of all or a fragment of an HPV RNA, wherein the HPV RNA cross-hybridizes to the HPV portion of clone pCD15 to greater than 50% under moderately stringent conditions, and
 wherein the HPV 52 DNA and HPV 52 RNA do not hybridize to DNA from HPV types 1 through 51 under stringent conditions.

19. The HPV hybridization probe as claimed in claim 18, wherein said hybridization probe contains the sequence of the HPV 52 non-protein encoding region between regions L1 and E6.

20. The HPV 52 hybridization probe as claimed in claim 18, wherein the HPV DNA is the HPV portion of clone pCD15 and the HPV RNA corresponds to the HPV portion of clone pCD15.

21. An HPV hybridization probe composition comprising
 (a) a member selected from the group consisting of
  (i) HPV 52 DNA labelled with a detectable label and
  (ii) HPV 52 RNA labelled with a detectable label,
 wherein the length of the HPV 52 DNA or HPV 52 RNA is between approximately 15 and 8000 nucleotide bases,
 wherein the HPV 52 DNA consists of all or a fragment of an HPV DNA, wherein the HPV DNA cross-hybridizes to the HPV portion of clone pCD15 to greater than 50% under moderately stringent conditions,
 wherein the HPV 52 RNA consists of all or a fragment of an HPV RNA, wherein the HPV RNA cross-hybridizes to the HPV portion of clone pCD15 to greater than 50% under moderately stringent conditions, and
 wherein the HPV 52 DNA and HPV 52 RNA do not hybridize to DNA from HPV types 1 through 51 under stringent conditions, and
 (b) DNA or RNA of at least one other HPV type labelled with a detectable label.

22. The HPV hybridization probe composition as claimed in claim 21, wherein said HPV hybridization probe composition contains the sequence of the HPV non-protein encoding region between regions L1 and E6.

23. The HPV 52 hybridization probe composition as claimed in claim 21, wherein the HPV DNA is the HPV portion of clone pCD15 and the HPV RNA corresponds to the HPV portion of clone pCD15.

24. A method for detecting HPV DNA or RNA comprising:
 (1) carrying out hybridization, under non-stringent conditions, with
  (a) a member selected from the group consisting of
   (i) HPV 52 DNA labelled with a detectable label, and
   (ii) HPV 52 RNA labelled with a detectable label,
  wherein the length of the HPV 52 DNA or HPV 52 RNA is between approximately 15 and 8000 nucleotide bases,
  wherein the HPV 52 DNA consists of all or a fragment of an HPV DNA, wherein the HPV DNA cross-hybridizes to the HPV portion of clone pCD15 to greater than 50% under moderately stringent conditions,
  wherein the HPV 52 RNA consists of all or a fragment of an HPV RNA, wherein the HPV RNA cross-hybridizes to the HPV portion of clone pCD15 to greater than 50% under moderately stringent conditions, and
  wherein the HPV 52 DNA and HPV 52 RNA do not hybridize to DNA from HPV types 1 through 51 under stringent conditions, and;
  (b) an unknown sample of DNA or RNA, and
 (2) assaying for the presence of hybridization so as to detect HPV DNA or RNA in said sample.

25. The method of claim 24, wherein the HPV DNA is the HPV portion of clone pCD15 and the HPV RNA corresponds to the HPV portion of clone pCD15.

26. A method for detecting HPV 52 DNA or RNA comprising:
 (1) carrying out hybridization, under stringent conditions, with
  (a) a member selected from the group consisting of
   (i) HPV 52 DNA labelled with a detectable label, and
   (ii) HPV 52 RNA labelled with a detectable label,
  wherein the length of the HPV 52 DNA or HPV 52 RNA is between approximately 15 and 8000 nucleotide bases,
  wherein the HPV 52 DNA consists of all or a fragment of an HPV DNA, wherein the HPV DNA cross-hybridizes to the HPV portion of clone pCD15 to greater than 50% under moderately stringent conditions,
  wherein the HPV 52 RNA consists of all or a fragment of an HPV RNA that cross-hybridizes to the HPV portion of clone pCD15 to greater than 50% under moderately stringent conditions, and
  wherein the HPV 52 DNA and HPV 52 RNA do not hybridize to DNA from HPV types 1 through 51 under stringent conditions, and;
  (b) an unknown sample of DNA or RNA, and
 (2) assaying for the presence of hybridization so as to detect HPV 52 DNA or RNA in said sample.

27. The method of claim 26, wherein the HPV DNA is the HPV portion of clone pCD15 and the HPV RNA corresponds to the HPV portion of clone pCD15.

* * * * *